United States Patent [19]

Aurora et al.

[11] 4,081,992
[45] Apr. 4, 1978

[54] APPARATUS FOR LOAD TESTING FOUNDATION SHAFTS

[75] Inventors: Ravi P. Aurora; Glyen D. Farmer, both of Houston, Tex.

[73] Assignee: Farmer Foundation Company, Inc., Houston, Tex.

[21] Appl. No.: 743,851

[22] Filed: Nov. 22, 1976

[51] Int. Cl.² ........................................... G01N 33/24
[52] U.S. Cl. ......................................................... 73/84
[58] Field of Search ................................. 73/84, 88 E

[56] References Cited

U.S. PATENT DOCUMENTS

| | | | |
|---|---|---|---|
| 2,697,937 | 12/1954 | Richards, Jr. | 73/84 |
| 3,054,285 | 9/1962 | Rousen | 73/84 |
| 3,946,601 | 3/1976 | Yizhaki | 73/84 |

*Primary Examiner*—Charles A. Ruehl
*Attorney, Agent, or Firm*—Bard, Springs, Jackson & Groves

[57] ABSTRACT

A reaction tie-down system for axially load testing foundation members is provided by removably interconnecting a plurality of high tensile strength bar members from a base plate within a concrete anchor shaft through an adaptor to load-carrying girders. Hydraulic jacks apply an axial load between the foundation shaft which is to be tested and the girders. The reaction force to this axial load is provided by the reaction tie-down system wherein the force is transmitted from the girder through the rods to the anchor shafts and through the anchor shafts to the surrounding soil. The bar members are arranged in a circular pattern for flexibly matching the number of bar members to the anticipated test load. The bar members threadly mate with the base plate and the adaptor and the bar members are removably encased within the concrete anchor shaft by flexible sheaths. All the components are, therefore, reusable except the embedded base plate assembly and flexible sheaths.

14 Claims, 4 Drawing Figures

APPARATUS FOR LOAD TESTING FOUNDATION SHAFTS

BACKGROUND OF THE INVENTION

This invention relates to load testing foundation shafts and more particularly to reaction tie-down systems used to provide reaction to axial test loads applied to foundation shafts.

Foundation shafts are used frequently in the construction of modern buildings to properly support the building foundation on various types of soils. Although the behavior of soils can be predicted to some extent, such behavior is not an exact science and actual tests must be conducted in the field to determine the load-bearing capabilities for a given foundation shaft design located in a particular site. The final number and location of foundation shafts needed to support a particular building can then be estimated from the test results. The test results are necessary not only to ensure an adequate margin of safety, but to inform the building contractor whereby an unnecessary number of foundation shafts are not drilled.

One conventional technique for measuring the load carrying capability of a given foundation shaft is the reaction system whereby an axial load is generated by jacks bearing against load-carrying reaction beams which transmit the load to reaction anchor shafts aligned with the test foundation shaft. In one conventional reaction test system design, a steel adaptor girder is aligned within the anchor shaft after the shaft has been drilled, and the anchor shafts are then filled with suitable reinforcing material and concrete.

The conventional apparatus is, however, time consuming and costly to assembly and use. These adaptor girders must be held in relatively precise vertical alignment while the concrete cures to prevent eccentric loading by the reaction beams. Further, a substantial portion of the girder is required to be imbedded in the concrete to obtain sufficient bond to prevent the girder from pulling loose from the anchor shaft during application of the test load. The final assembly between a girder support system and the adaptor girders has to be performed on-site, and the mating bolt holes custom drilled to precisely align the load-carrying members. If the adaptor girder has not been aligned with sufficient precision in the first instance, it is apparent that no correction can be obtained once the concrete has cured in place. Additionally, at the conclusion of the testing, additional time and labor is required to remove the exposed portion of the adaptor girder and material costs are increased by having to leave the imbedded portion of the adaptor girder in place in the cast concrete anchor shaft.

These disadvantages of the prior art are overcome by the present invention, however, and an improved reaction test system is provided for axially loading foundation shaft members.

SUMMARY OF THE INVENTION

In a preferred embodiment of the present invention, a reaction tie-down system is provided by a plurality of high tensile strength bar members which transmit axial reaction forces from an adaptor assembly connection with the load-carrying girders to a base plate imbedded in a concrete anchor shaft further transferring the load forces to the reaction between the anchor shaft and the surrounding soil. The bar members are arranged in a circular pattern for flexibly matching the number of bar members to the anticipated axial test load. The bar members threadedly mate with nuts to the adaptor assembly and to the base plate. Further, the bar members are encased in a flexible tubing and enclosed beneath the base plate by a locking cup. The locking cup serves to prevent rotation of the bottom nut member once the locking cup is installed on the base plate and to protect the bar members from the surrounding concrete or soil.

When the load test is completed, the adaptor member is simply unbolted from the load carrying girders and moved from around the high strength bars. The high strength bars may then be rotated out of engagement with the bottom nut members and removed from inside the flexible sheaths which protect the bars from the surrounding concrete. In this manner, only the bottom base plate and the low cost flexible sheaths remain behind in the anchor shaft.

It is a feature of the present invention that the need for precise alignment between the load-carrying girder and the reaction system is reduced.

It is another feature of the present invention that tie-down components of the reaction test apparatus may be re-used.

It is yet another feature of the present invention that the material and labor costs required to run axial load tests on foundation shafts are reduced.

It is a feature of the present invention to permit off-site assembly of the anchor shaft reaction system components.

It is yet another feature of the present invention to provide design flexibility in installing only the number of bar members required to conduct a particular load test.

These and other features and advantages of the present invention will become apparent from the following detailed description, wherein references are made to the figures in the accompanying drawings.

IN THE DRAWINGS

DETAILED DESCRIPTION OF THE DRAWINGS

Figure 1:
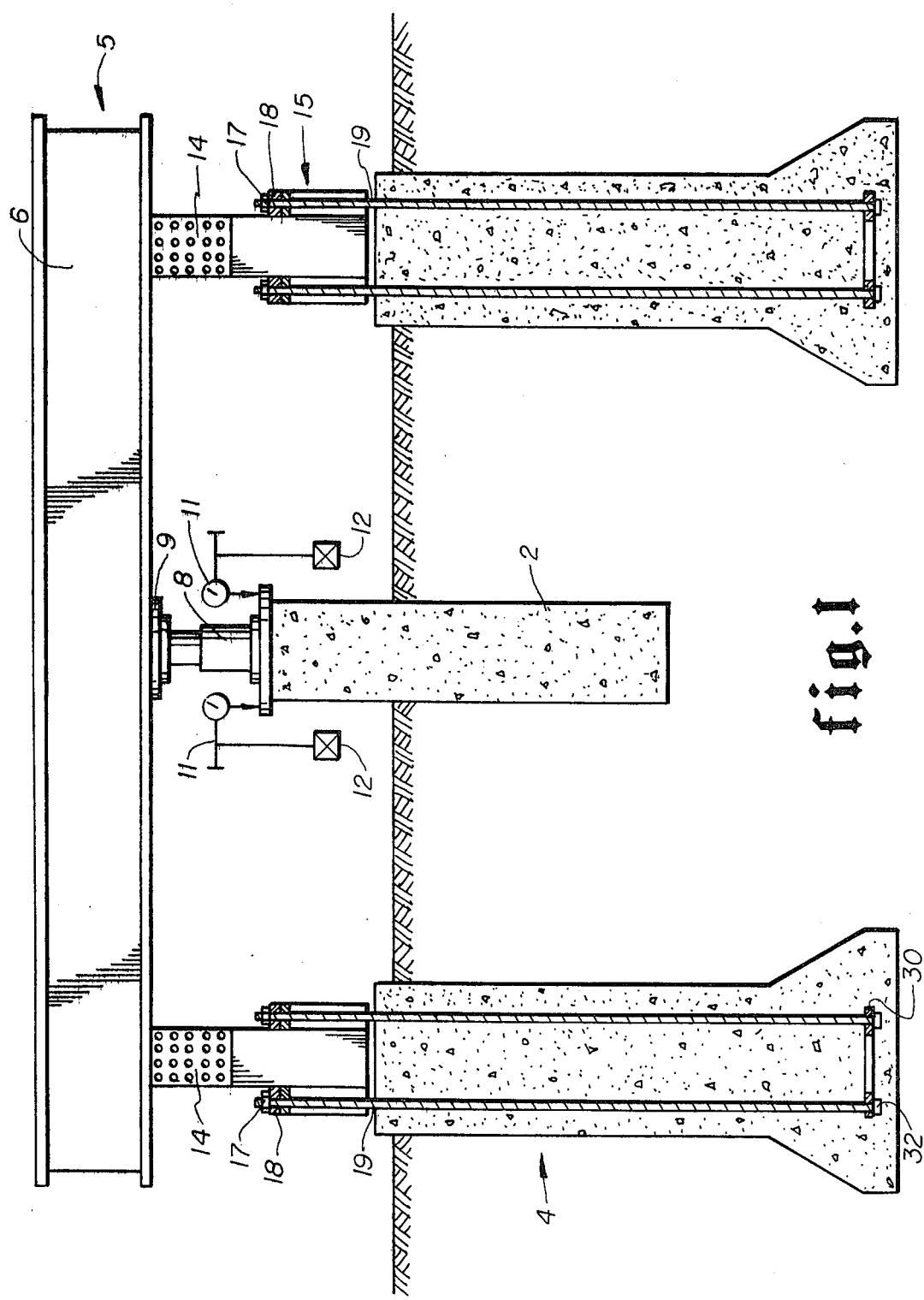
FIG. 1 is a simplified functional diagram of the foundation shaft axial test reaction tie-down system.

Referring now to FIG. 1, there may be seen a functional diagram of the reaction test assembly used to axially load test a foundation shaft 2. Test shaft 2 is first designed and constructed to carry the anticipated design loads. Two reaction force anchor shafts 4 are then drilled in alignment with the test shaft 2 so as to eliminate eccentric loading. Parallel plate girders 6 span anchor shafts 4. A hydraulic jack 8 is in place on test shaft 2 beneath plate girder 6. Bearing plate 9 is disposed between hydraulic jack 8 and plate girders 6 in order to distribute the applied load over the bottom flanges of plate girders 6. Anchor posts 14 depend from plate girders 6 above the location of anchor shafts 4. The above components comprise a conventional reaction beam system 5. It should be noted that beam means other than plate girders, or a truss system may be used to transmit reaction forces within the scope of the present invention.

The reaction beam system 5 is then connected with the reaction tie-down assembly which is the subject of the present invention by interconnecting anchor posts 14 with adaptor assembly 15. High tensile strength bars 19 extend from adaptor assembly 15 to base plate 30 which transmits the reaction forces from the tie-down assembly to anchor shaft 4. Bar 19 is threadingly engaged with nut 17 which rests on bearing washer 18 for transmitting the load from adaptor assembly 15 to bar 19. Bar 19 is further threadingly engaged with nut 35 beneath base plate 30 and surrounded by locking cup 32. Locking cup 32 acts to prevent rotation of nut 35 when placed around nut 35.

Referring again to FIG. 1, other conventional features may also be seen. Displacement dial gauges 11 are aligned with respect to reference beams 12 so as to detect any movement of test shaft 2 under application of the axial load transmitted to test shaft 2 via the reaction test assembly.

Figure 2:
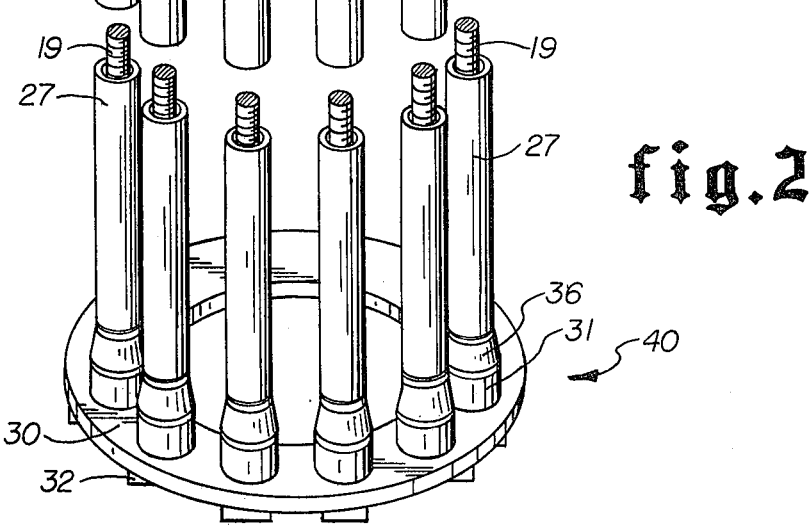
FIG. 2 is an illustration of an assembled reaction system tie-down assembly according to one embodiment of the present invention.

Referring now to FIG. 2, there may be seen an assembled reaction tie-down system ready for installation in a drilled anchor shaft. Adaptor assembly 15 is attached to high strength bar members 19 by nuts 17 seated on bearing washers 18 which, in turn, rest on adaptor plate 24. This initial assembly of adaptor assembly 15 with bar members 19 may be done for the purpose of lifting the assembly and for installation into the drilled anchor shaft. The vertical alignment and vertical elevation of connecting member 21 may then be suitably corrected by adjustment of nuts 17 after the concrete for the anchor shafts has been poured and has set.

Bar members 19 further engage base plate assembly 40, extending through base plate 30 into locking caps 32 for threadingly engaging nuts as hereinbelow described. Flexible sheaths 27 surround bar members 19 throughout that portion of the anchor shaft which is filled with concrete. Flexible sheaths 27 extend into pipe stubs 31 which are attached to base plate 30. The annular space between the flexible sheaths 27 and pipe stubs 31 is sealed with wax and flexible tape 36 further seals the junction of the flexible sheath and the pipe stub.

The reaction tie-down assembly is then placed in the anchor shaft, the anchor shaft is filled with concrete in a conventional manner, and the concrete is allowed to cure. Connecting member 21 is then adjusted to align holes 22 with mating holes in anchor posts 14 of the reaction beam system 5 shown in FIG. 1. At the conclusion of the axial tests, bar members 19 are rotated out of engagement with the nuts in locking cups 32, adaptor assembly 15 is unbolted from reaction system 5 and adaptor assembly 15 and bar members 19 are removed from the anchor shaft to be reused in subsequent load tests. The recovery of substantially all the steel members from the anchor shaft results in considerable cost savings over the method where an adaptor girder was used and substantially all the girder remained behind in the anchor shaft.

Referring again to FIG. 2, there may be seen adaptor assembly 15 according to one embodiment of the present invention. Bar members 19 extend through adaptor plate 24 into threading engagement with nuts 17. Nuts 17 rest on bearing washers 18 which act to distribute the load forces over adaptor plate 24. Stiffener ribs 25 are provided to prevent deflection of adaptor plate 24 as the bar members 19 are loaded. Connecting member 21 extends upwardly from adaptor plate 24 for interconnection with the reaction beam system 5, described hereinabove, and defines a pattern of holes 22 adapted to match the corresponding pattern on conventional anchor posts 14. Holes 22 are drilled for precise alignment with the mating anchor posts 14, but this alignment need only to be done once since adaptor assembly 15 may be reused. The flexibility of bar members 19 permit adaptor assembly 15 to be easily aligned to a vertical position and further adjusted to a variety of vertical elevations by means of nuts 17. Nuts 17 may also be positioned beneath adaptor assembly 15 to aid in temporarily supporting adaptor assembly 15 during vertical alignment with the reaction beam assembly.

In an alternate embodiment of the adaptor assembly, the bolted connecting member 21 is replaced with a yoke assembly. The yoke assembly is substantially I-shaped wherein the load carrying girders are confined with the elongated flanges depending from the body portion. The body portion depends from adaptor plate 24 in the same manner as connecting member 21, but bolting is not required to complete the on-site assembly to the load-carrying girders.

Referring yet again to FIG. 2, there may be seen openings for bar members 19 disposed in base member 24 in a circular pattern about connecting member 21. Stiffener ribs 25 are provided near each opening as hereinabove discussed. The circular pattern provided for the openings for bar members 19 allows the number of bar members 19 to be varied as a function of the axial load to be applied in a particular test situation. Symmetric loading of the adaptor assembly 15 is easily obtained as a result of the spacing of the openings and the circular pattern. The maximum number of openings is such as to accommodate a number of commercially available high strength steel bars 19 which match the loads that can be obtained from the largest commercially available hydraulic jacks. The diameter of each opening disposed about the circular pattern is somewhat larger than the diameter of bar members 19 to permit some angular displacement of bar members 19 with respect to the axis of the opening.

Figure 3:
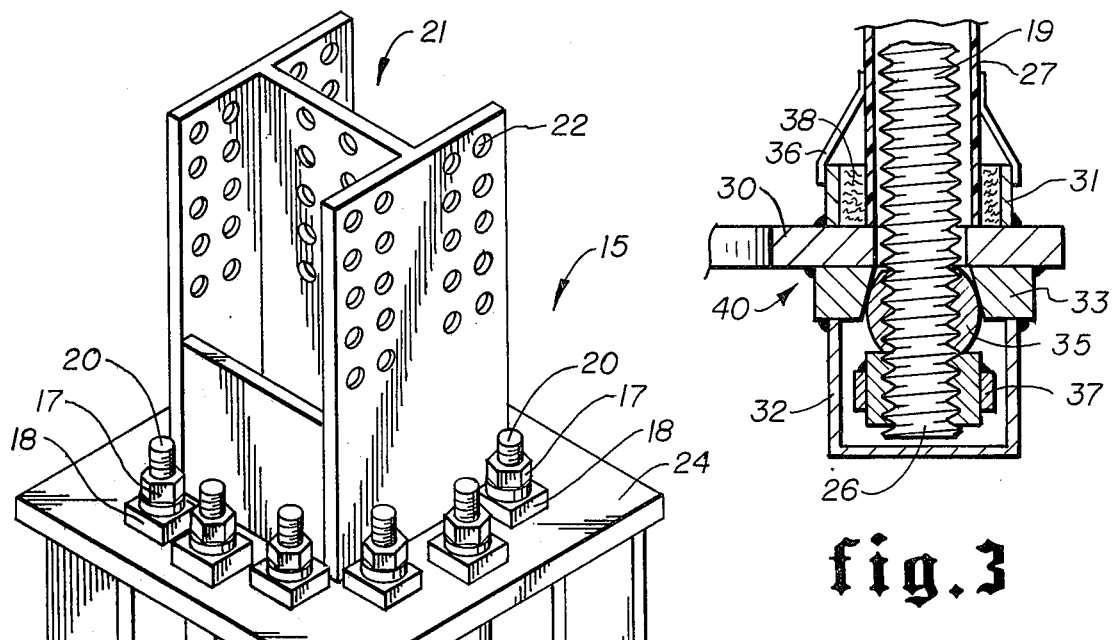
FIG. 3 is a cross-section of the base plate assembly.

Referring now to FIG. 3, there may be seen a cross-section of base plate assembly 40. Base plate 30 may be a ring-shaped plate that has a number of holes through it to match the number of high strength bar members 19 to be used and disposed in the circular pattern defined by adaptor plate 24. A bar member 19 passes through each opening and base plate 30 to a point beneath base plate 30. A theaded bottom end 26 is provided on bar 19 for threadingly engaging nut 35. A bearing plate 33 may be provided whereby nut 35 transmits the reaction forces through bearing plate 30.

It will be seen from FIG. 3 that a lock cup 32 is provided which covers the end 26 of bar member 19. Locking cup 32 not only prevents the surrounding concrete from engaging the threaded end of bar member 19, but also prevents rotation of nut 35 when locking cup 32 is attached adjacent bearing plate 33. In one embodiment, a first locking bar 37 is attached to nut 35 by some convenient means such as welding and effectively prevents rotation of nut 35 so as to allow bar member 19 to be disengaged from nut 35 from a remote location.

Referring again to FIG. 3, there may be further seen a means for further protecting bar member 19 from the surrounding concrete. A pipe stub 31 is placed above each opening in base plate 30, the pipe stub 31 being somewhat larger than the diameter of flexible sheath member 27. Each bar member 19 is surrounded by flexible sheath member 27 from a level above the top of the anchor shaft until at least a level adjacent stub 31. Prior to installing the reaction tie-down assembly in the anchor shaft, a molten substance such as wax is poured in the annular space 38 between the outside of flexible sheath 27 and the inner diameter of pipe stub 31. When the molten substance solidifies, concrete is effectively blocked from entering the interior of locking cup 32 beneath base plate 30. To further seal the annulus 38, a wrapping 36 may be adhesively affixed about the top of the annular space.

Figure 4:
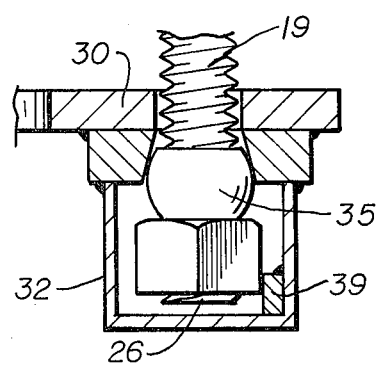
FIG. 4 is a cross-sectional view of an alternate embodiment of the locking cup assembly.

Referring now to FIG. 4, there may be seen another embodiment of locking cup 32. In this embodiment, locking bar 39 is attached to locking cup 32 and may be disposed parallel to one face of nut 35 to effectively prevent rotation of nut 35 once locking cup 32 is installed around nut 35. Although only two varieties of locking cups are illustrated, alternate locking arrangements may be utilized within the spirit and scope of the present invention.

Numerous variations and modifications may obviously be made in the structure herein described without departing from the present invention. Accordingly, it should be clearly understood that the forms of the invention herein described and shown in the figures of the accompanying drawings are illustrative only and are not intended to limit the scope of the invention.

What is claimed is:

1. An apparatus for axial load testing foundation shafts, comprising
   a plurality of concrete anchor shafts aligned with a foundation shaft to be tested,
   beam means spanning between said plurality of anchor shafts and over said foundation shaft,
   means for applying an axial load between said beam means and said foundation shaft, and
   a tie-down assembly formed within and substantially removable from the interior of each of said anchor shafts for transferring reaction forces from said means for applying an axial load to said anchor shafts, including
   base means fixedly connected within said anchor shaft,
   a plurality of tension members removably connected to said base means and extending upwardly through said anchor shaft, and
   adaptor means for removably connecting said tension members to said beam means.

2. The apparatus described in claim 1, wherein said tension members comprise a plurality of high tensile strength bars threadingly connected to said base means and said adaptor means and arranged in a generally spaced-apart and symmetric circular pattern in said one anchor shaft.

3. The apparatus described in claim 2, wherein said adaptor means further comprises
   an adaptor plate defining a plurality of holes therethrough arranged in a corresponding spaced-apart circular pattern for receiving said tension members,
   a plurality of stiffener ribs located beneath said adaptor plate for supporting said adaptor plate against reaction load forces applied by said tension members, and
   a connecting portion depending upwardly from said adaptor plate for alignment and interconnection with said beam means.

4. The apparatus described in claim 3, wherein said base means further comprises
   a base plate defining a plurality of openings therethrough in a corresponding spaced-apart pattern for receiving said tension members, and
   means for removably engaging said tension members.

5. The apparatus described in claim 4, wherein the number of said bars is functionally related to the axial load applied to said foundation shaft.

6. The apparatus described in claim 5, wherein said means for removably engaging said tension members further includes
   a plurality of protective cylinders concentric with said plurality of openings in said base plate and extending vertically upward from said base plate,
   a plurality of nuts for threadedly engaging said tension members beneath said base plate,
   locking means for preventing rotation of said nuts, and
   sheath means extending upwardly from said protective cylinders for shielding said tension members from the concrete forming said anchor shaft.

7. The apparatus described in claim 6, wherein said sheath means includes a plastic pipe sized to enclose said tension members and vertically extending to a level above said concrete in said anchor shaft.

8. The apparatus described in claim 9, wherein said locking means includes
   an enclosing cup extending beneath said base plate for shielding said nut from said concrete, and
   a lock bar depending from said nut and along one side of said cup for opposing rotation of said nut in said cup.

9. The apparatus described in claim 7, wherein said locking means includes
   an enclosing cup extending beneath said base plate for shielding said nut from said concrete, and
   a lock bar depending interiorly from said cup and along one side of said nut for opposing rotation of said nut in said cup.

10. In a system for reacting to axial load forces applied to test a foundation shaft, a hydraulic jack, a reaction beam, and a plurality of concrete anchor shafts, an improved reaction tie-down apparatus, comprising
    base means fixedly connected within one of said anchor shafts,
    a plurality of tension members removably connected to said base means and extending upwardly through said one anchor shaft, and
    adaptor means for removably connecting said tension members to said reaction beam.

11. The apparatus described in claim 10, wherein said tension members comprise a plurality of high tensile strength bars threadingly connected to said base means and said adaptor means and arranged in a generally spaced-apart and symmetric circular pattern in said one anchor shaft.

12. The apparatus described in claim 11, wherein said adaptor means further comprises
    an adaptor plate defining a plurality of holes therethrough arranged in a corresponding spaced-apart circular pattern for receiving said tension members,
    a plurality of stiffner ribs located beneath said adaptor plate for supporting said adaptor plate against reaction load forces applied by said tension members, and a connecting portion extending upwardly from said adaptor plate for alignment and interconnection with said reaction beam.

13. The apparatus described in claim 12, wherein said base means further comprises
   a base plate defining a plurality of openings therethrough in a corresponding spaced-apart circular pattern for receiving said tension members,
   a plurality of protective cylinders concentric with said plurality of openings in said base plate and extending vertically upward from said base plate,
   a plurality of nuts for threadedly engaging said tension members beneath said base plate,
   locking means for preventing rotation of said nuts, and
   flexible sheath means extending upwardly from said protective cylinders for shielding said tension members from the concrete forming said anchor shaft.

14. In a system for reacting to axial load forces applied to test a foundation shaft, a hydraulic jack, a reaction beam and anchor post and a plurality of concrete anchor shafts, an improved reaction tie-down apparatus comprising
   a base plate fixedly connected within one of said anchor shafts and defining a plurality of openings therethrough generally in a spaced-apart and symmetric circular pattern about said base plate,
   a plurality of tension members extending upwardly from below said base plate and through said openings to a level above said concrete in said one anchor shaft,
   a first plurality of nuts for threadingly engaging the bottom portion of said tension members,
   a plurality of enclosing cups extending beneath said first nuts for opposing rotation of said first nuts and for shielding said tension members from said concrete in said anchor shafts,
   a plurality of sheaths enclosing said plurality of tension members for shielding said tension members from said concrete in said anchor shafts,
   a rigid adaptor plate defining a plurality of corresponding spaced-apart openings for said tension members to pass therethrough for aligning with said openings in said base plate,
   a second plurality of nuts for threadingly engaging the top portion of said tension members extending above said adaptor plate, and
   a connecting portion depending upwardly from said adaptor plate for alignment and interconnection with said anchor post on said reaction beam to transmit reaction forces from said reaction beam to said tension members.

* * * * *